(12) United States Patent
Samadani et al.

(10) Patent No.: US 12,318,540 B2
(45) Date of Patent: Jun. 3, 2025

(54) PREDICTION OF VENTILATOR-ASSOCIATED EVENTS (VAEs)

(71) Applicant: KONINKLIJKE PHILIPS N.V., Eindhoven (NL)

(72) Inventors: Ali Akbar Ahmad Samadani, Cambridge, MA (US); Ikaro Garcia Araujo Da Silva, Cambridge, MA (US); Francesco Vicario, Cambridge, MA (US); Cornelis Van Zon, Cambridge, MA (US); Taiyao Wang, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 838 days.

(21) Appl. No.: 17/412,675

(22) Filed: Aug. 26, 2021

(65) Prior Publication Data

US 2022/0184331 A1 Jun. 16, 2022

Related U.S. Application Data

(60) Provisional application No. 63/124,978, filed on Dec. 14, 2020.

(51) Int. Cl.
*A61M 16/00* (2006.01)
*G16H 10/60* (2018.01)
(Continued)

(52) U.S. Cl.
CPC ...... *A61M 16/024* (2017.08); *A61M 16/0051* (2013.01); *G16H 10/60* (2018.01);
(Continued)

(58) Field of Classification Search
CPC ............ A61M 16/024; A61M 16/0051; A61M 2230/40; A61M 2016/0027;
(Continued)

(56) References Cited

U.S. PATENT DOCUMENTS

2011/0029248 A1* 2/2011 Saeed ............... A61M 16/0051
702/19
2014/0006041 A1 1/2014 Steinhauer
(Continued)

OTHER PUBLICATIONS

Cocoros, N. et al.,"Ventilator-associated events and their prevention." Infectious Disease Clinics, 30(4):887-908, 2016.
(Continued)

*Primary Examiner* — Victoria Murphy
*Assistant Examiner* — Tina Zhang
(74) *Attorney, Agent, or Firm* — Daniel H. Brean; Andrew M. Gabriel (57) ABSTRACT

Described herein are methods, devices and systems for predicting ventilator associated events (VAEs). In an example, data of a patient including one or more features useful in predicting VAEs is accessed and the features are extracted. The extracted features are evaluated automatically to determine a probability that a VAE will occur. If it is determined, based on the evaluating, that a VAE has a probability of occurring that exceeds a threshold, an indication that the VAE is predicted to occur is provided. Other examples are disclosed and claimed.

7 Claims, 7 Drawing Sheets

(51) Int. Cl.
*G16H 40/67* (2018.01)
*G16H 50/30* (2018.01)

(52) U.S. Cl.
CPC ............ *G16H 40/67* (2018.01); *G16H 50/30* (2018.01); *A61M 2230/40* (2013.01)

(58) Field of Classification Search
CPC .. A61M 2016/1025; A61M 2205/3553; A61M 2205/3584; A61M 2205/3592; A61M 2205/502; A61M 2205/52; A61M 2205/581; A61M 2205/583; A61M 2230/06; A61M 2230/201; A61M 2230/205; A61M 2230/207; A61M 2230/208; A61M 2230/30; A61M 2230/42; A61M 2230/50; A61M 2230/62; A61M 16/026; G16H 10/60; G16H 40/67; G16H 50/30; G16H 20/40; A61B 5/7264; A61B 5/7275
USPC .......................................................... 705/2
See application file for complete search history.

(56) References Cited

U.S. PATENT DOCUMENTS

2014/0230819 A1  8/2014  Rawlins
2018/0193579 A1  7/2018  Hanrahan

OTHER PUBLICATIONS

NHSN Patient Safety Component Manual, Jan. 2019.
2019 NHSN Ventilator-Associated Event (VAE) Checklist, Centers for Disease Control and Prevention.
Hayashi, Y. et al., "Toward improved surveillance: The impact of ventilatorassociated complications on length of stay and antibiotic use in patients in intensive care units." Clinical Infectious Diseases, 56(4):471-477, 2013.
International Search Report for PCT/EP2021/084685 filed Dec. 8, 2021.

* cited by examiner

PREDICTION OF VENTILATOR-ASSOCIATED EVENTS (VAEs)

CROSS-REFERENCE TO RELATED APPLICATIONS

This patent application claims the priority benefit under 35 U.S.C. § 119(e) of U.S. Provisional Application No. 63/124,978, filed on Dec. 14, 2020, the contents of which are herein incorporated by reference.

FIELD OF THE INVENTION

The subject matter described herein generally relates to automated techniques for using medical data to predict ventilator-associated events (VAEs). Certain subject matter described relates to predicting ventilator-associated conditions (VACs).

BACKGROUND OF THE INVENTION

Patients receiving mechanical ventilation (MV) are at high risk of developing complications including ventilator-associated pneumonia (VAP), acute respiratory distress syndrome (ARDS), pulmonary embolism, barotrauma, and pulmonary edema. Every year 10% of 800,000 mechanically ventilated patients in the US develop ventilator-associated complications. These complications lead to a number of negative outcomes for the patients (e.g., longer MV and intensive care unit (ICU) stay as well as increased risk of disability and death). These complications also pose significant burdens on the healthcare system.

Prior to 2013, National Healthcare Safety Network (NHSN) surveillance was limited to VAP based on NHSN Pneumonia (PNEU) criteria. NHSN Pneumonia (PNEU) criteria are subjective for VAP detection as they heavily rely on radiologist judgment of chest X-rays. Furthermore, NHSN PNEU criteria offer multiple pathways for different patient populations, include non-specific and insensitive criteria e.g., "change in the character of sputum" and "worsening cough," and have poor correlation with histologic pneumonia.

To address these limitations and help streamline tracking of ventilator-associated complications, the US Center for Disease Control and Prevention (CDC) introduced a three-tiered guideline for surveillance of ventilator-associated events (VAEs) in 2013. The three-tiers of VAE are: (1) ventilator-associated condition (VAC), characterized as deterioration in respiratory status after a period of stability or improvement on the ventilator; (2) infection-related ventilator-associated complication (IVAC), characterized as evidence of infection or inflammation; and (3) possible VAP (PVAP), characterized as laboratory evidence of respiratory infection.

SUMMARY OF THE INVENTION

Various embodiments provide methods, devices, products and systems for predicting ventilator associated events (VAEs). In an example, data of a patient including one or more features useful in predicting VAEs are accessed and the features are extracted. The extracted features are evaluated automatically to determine a probability that a VAE will occur. If it is determined, based on the evaluating, that a VAE has a probability of occurring that exceeds a threshold, an indication that the VAE is predicted to occur is provided.

In summary, one embodiment provides a method of predicting ventilator associated events, including: accessing, using a processor, data of a patient comprising one or more features; evaluating, using a processor, the one or more features to determine a probability that a ventilator-associated event (VAE) will occur; determining, based on the evaluating, that a VAE has a probability of occurring that exceeds a threshold; and providing, using an output device, an indication that the VAE is predicted to occur.

Another embodiment provides a system for predicting ventilator associated events, comprising: an output device; a processor operatively coupled to the output device; and a memory operatively coupled to the processor, the memory comprising processor-executable code comprising: code that accesses data of a patient comprising one or more features; code that evaluates the one or more features to determine a probability that a ventilator-associated event (VAE) will occur; code that determines, based on evaluation of the one or more features, that a VAE has a probability of occurring that exceeds a threshold; and code that provides, using an output device, an indication that the VAE is predicted to occur.

A further embodiment provides a ventilator, comprising: a non-transitory storage medium having processor-executable code comprising: code that accesses data of a patient comprising one or more features; code that evaluates the one or more features to determine a probability that a ventilator-associated event (VAE) will occur; code that determines, based on evaluation of the one or more features, that a VAE has a probability of occurring that exceeds a threshold; and code that provides, using an output device, an indication that the VAE is predicted to occur.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION OF EMBODIMENTS

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the claims, but is merely representative of those embodiments.

Reference throughout this specification to "embodiment(s)" (or the like) means that a particular feature, structure, or characteristic described in connection with the embodiment is included in at least one embodiment. Thus, appearances of the phrases "according to embodiments" or "an embodiment" (or the like) in various places throughout this specification are not necessarily all referring to the same embodiment.

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware. The term "about" or "approximately" as used herein includes conventional rounding of the last significant digit.

Furthermore, the described features, structures, or characteristics may be combined in any suitable manner in one or more embodiments. In the following description, numerous specific details are provided to give a thorough understanding of example embodiments. One skilled in the relevant art will recognize, however, that aspects can be practiced without one or more of the specific details, or with other methods, components, materials, etc. In other instances, well-known structures, materials, or operations are not shown or described in detail to avoid obfuscation.

As the entry point to describing a ventilator associated event (VAE), ventilator associated conditions (VACs) have the highest rates followed by infection-related ventilator associated complications (IVACs) and possible ventilator associated pneumonia (PVAP). While improvements in determining when VAEs have occurred have been made, e.g., by introducing objective criteria, the CDC three-tiered guidelines are only able to detect VAEs after they happen. For instance, the criteria behind the CDC guidelines allow for VAC detection between 24 and 48 hours after the complication has started (namely worsening of oxygenation).

In an embodiment, medical data is utilized to automate the prediction of VAEs, i.e., in advance of the development of complication(s). This permits healthcare providers to be apprised of predicted worsening of conditions for MV patients and proactively address the same. In an embodiment, a system uses a patient profile, for example including demographics, medical records available in an electronic health record (EHR) or an electronic medical record (EMR), ongoing ventilator settings, clinical observations, and lab results to estimate risk of developing VAEs. In an embodiment, a system may be used prior to or at the onset of MV to generate an estimated risk of developing VAEs, during MV to generate an ongoing estimated risk of developing VAEs, or a suitable combination of the foregoing. The resulting risk scores may be used to trigger notifications to caregivers along with recommendation on interventions. These notifications may be in the form of indications, e.g., alarms added to patient's medical records accessible by caregivers through a medical records management portal or displayed in an intensive care unit (ICU) monitor (e.g., a central station, a bedside physiological monitor or a ventilator display screen). Additionally, an alarm may be activated according estimated risk scores and accompanied with a display of the timeline of events and patient's status used to predict the occurrence of a VAE.

An embodiment uses a model based on the CDC three-tiered guidelines for determining VAEs, as these are suited for automation. In an embodiment, the prediction model utilizes the CDC VAE definitions to automatically generate labels for training. In other embodiments, other guidelines, definitions or protocols may be utilized. For example, updates and changes to the CDC VAE definition may require re-generation of training labels, and thus re-training of the prediction model. Changes may include adaption of VAE guidelines for a different patient population such as the PedVAE guidelines for the pediatric population in which $F_iO_2$ and mean airway pressure (MAP) are used to track VAEs. This process may be semi-automated, with models upgraded with the latest CDC guidelines being pushed as part of ventilator software upgrades. An embodiment promotes accurate and continuous surveillance of MV patients while reducing labor cost associated with surveillance. Automation also helps to reduce missing cases or misclassified cases, e.g., due to human error or biases. This promotes timely or urgent interventions upon prediction or detection of VAEs.

The description now turns to the figures. The illustrated example embodiments will be best understood by reference to the figures. The following description is intended only by way of example and simply illustrates certain selected example embodiments representative of the invention, as claimed.

Figure 1:
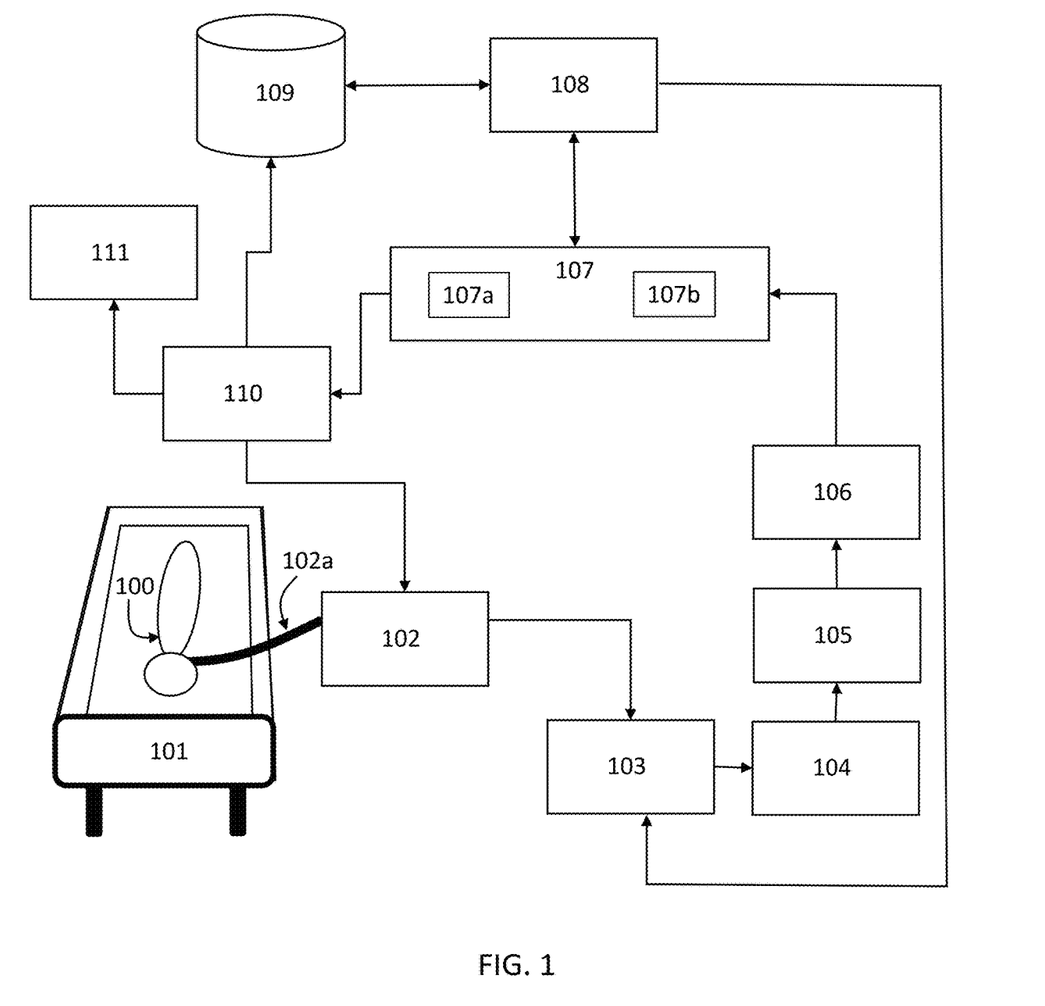
FIG. 1 illustrates an example system for automatically predicting VAEs.

Referring to FIG. 1, an example system is illustrated for automatically predicting VAEs. In the example of FIG. 1 a system includes a ventilator 102 that provides invasive mechanical ventilation via an oxygen delivery system 102a, e.g., including a breathing tube, to a patient 100. The ventilator 102 is a source for data useful in making VAE predictions and is therefore communicatively coupled to a data acquisition module 103, e.g., where a module may be a module of executable code configured to operate as described herein. For example, the ventilator 102 may provide data related to ventilator settings, such as positive end-expiratory pressure (PEEP) and fraction of inspired oxygen ($F_iO_2$), which may be used by an automated prediction system as further described herein.

The data acquisition module 103 communicates with the ventilator 102 and electronic medical record (EMR) or electronic health record (EHR) 108 to retrieve data recent and long-term patient chart for a patient 100. For example, the data acquisition module 103 may retrieve or access ventilator settings data, ventilation type and mode, lab results, and a patient's physiological data, along with a patient's demographics, comorbidities, diagnoses and the like. The data acquisition module 103 may use standard protocols and APIs, e.g., Fast Healthcare Interoperability Resources (FHIR), to communicate and extract data from EMR or EHR 108, a bedside physiological monitor 111, ventilator 102, etc.

The data acquisition module 103 may be configured to receive data periodically, continuously or may dynamically adjust its data acquisition. In an embodiment, the system uses the data by segmenting it, processing it, and extracting features from the resulting segments for evaluation according to a machine learning or artificial intelligence model, e.g., a trained classifier as described herein. In an embodiment, certain data may be used to adjust or change the processing, e.g., ventilator mode data such as indications of high frequency ventilation (HFV), extracorporeal life support, or paracorporeal membrane oxygenation are exclusion criteria for a VAE, as VAEs are only expected to occur on certain invasive ventilator modes.

Figure 2A:
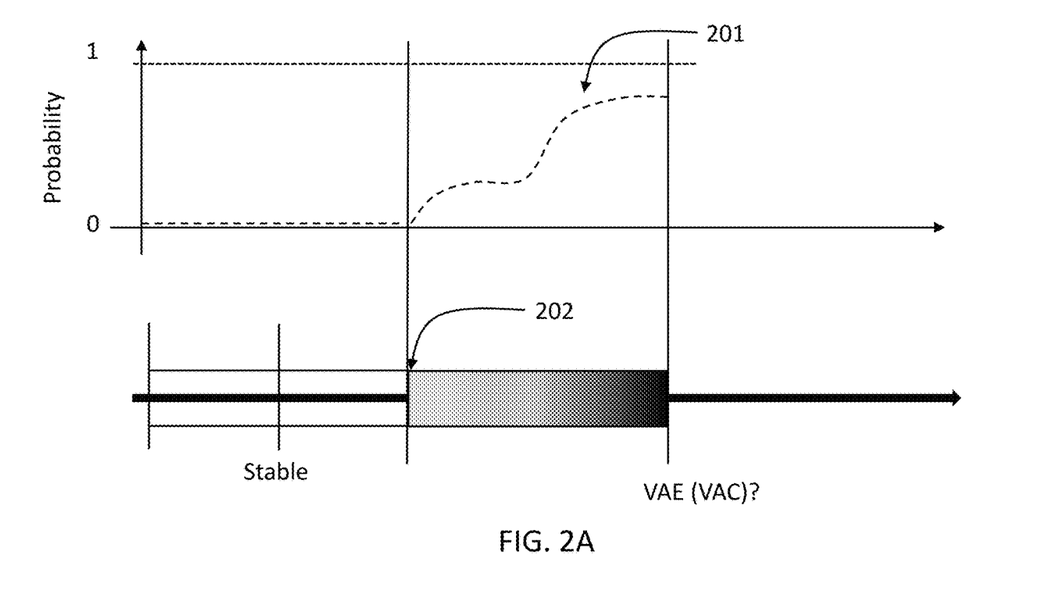
FIG. 2A illustrates an example time course for VAE evaluation and prediction.

As shown in FIG. 2A, this model can be used to calculate and monitor the probability of a VAE, e.g., a VAC, and to provide a prediction as to when the event, e.g., a VAC, is predicted to occur. The process may include continuously or periodically determining the VAC probability using a VAC score 201 that represents the probability of a VAC occurring in the future (coming hours or days) (dashed line in FIG. 2A). In one embodiment, the system is configured to define an event window encompassing the event, e.g., VAC, after a trigger event. For the purpose of estimating the risk of the event, the prediction model is configured to consider the event active in its corresponding event window.

In an embodiment that follows the aforementioned CDC guidelines for defining the VAE events, a prediction model may begin providing prediction scores once it detects a stability period immediately followed by a trigger event such as an oxygen worsening (OW) event as described by CDC VAE detection guidelines. FIG. 2A illustrates an example of prediction initiation for a VAC case. In the embodiment represented in FIG. 2A, the risk of VAE is 0% until the conditions defining oxygenation worsening are met. In other embodiments, prediction (risk >0%) may begin right at the detection of a stability period of two days as defined by the CDC. In the example of FIG. 2A, the trigger event 202 follows a two day stability period with respect to patient scored data, i.e., VAC score is stable for two days. If a trigger condition occurs, e.g., at 202, such as an oxygen worsening indication, the system may produce a prediction time for an impending VAC event, e.g., based on the VAC score exceeding a predetermined amount.

Figure 2B:
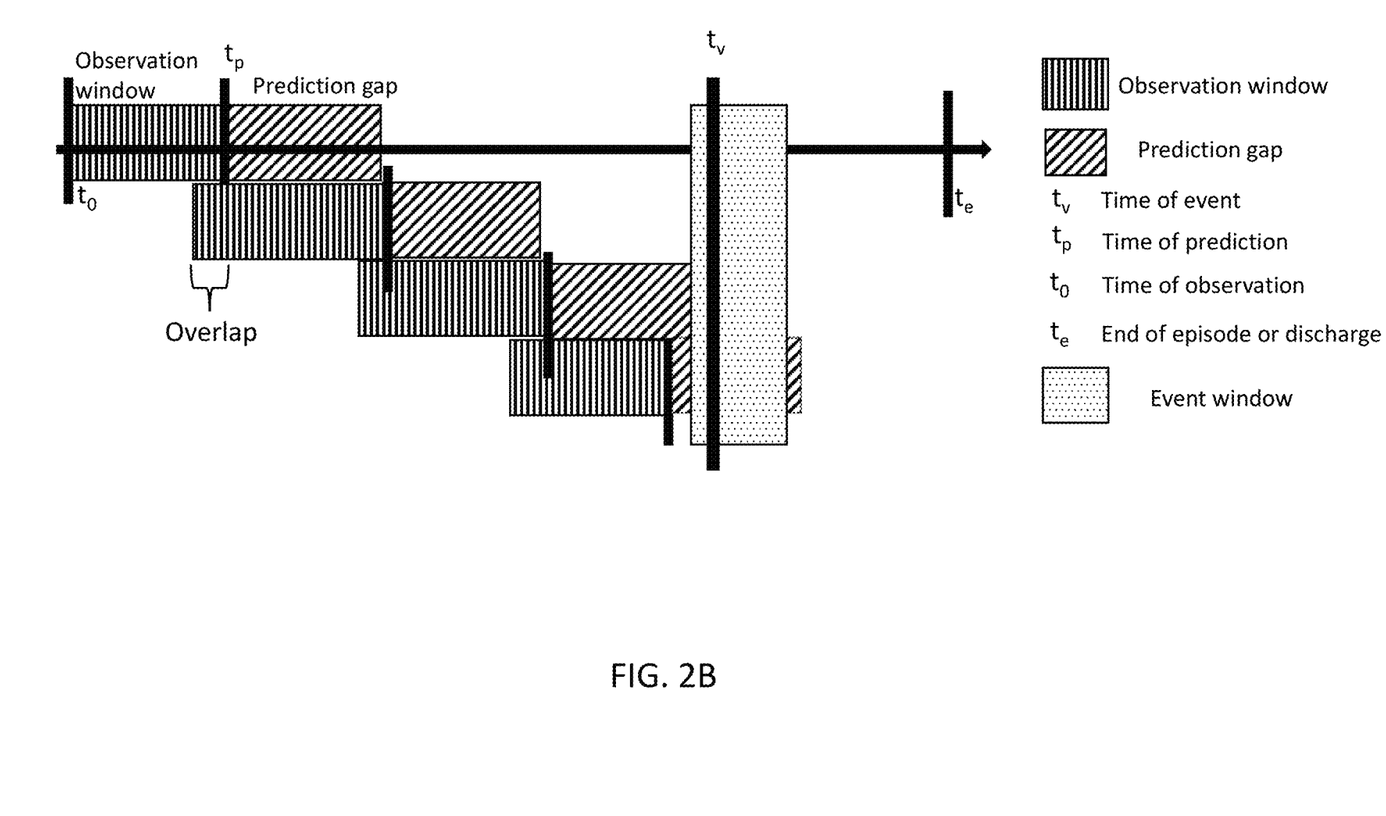
FIG. 2B illustrates an example of data segmentation.

Referring to FIG. 2B, in order to provide an event probability score, e.g., a VAC score, and associated event prediction, a data segmentation module 104 receives data streams representing ventilator settings, patient physiology, etc., and splits the streams into windows (observation windows) representing subsequent observations with or without overlap between successive windows. As illustrated in the example of FIG. 2B, each observation window constitutes an observation sample based on which an occurrence of VAE is predicted. The prediction gap (i.e., indicating how far in advance an impending VAE event can be predicted) is illustrated in the example in FIG. 2B.

In an embodiment there are four parameters that govern a segmentation process: 1) observation window duration, 2) the amount of overlap (overlap), 3) prediction gap duration, and 4) event window duration. How far in advance a VAE can be reliably predicted is referred to as prediction gap duration. A temporal offset around a VAE event may be constructed as a window (event window), bounding the time around the impending event time ($t_v$). Thus, at observation time ($t_o$), an observation window (from $t_o$ to $t_p$) is used to predict if a VAE is likely to occur after the prediction gap. For each time a prediction is made ($t_p$), it is evaluated whether VAE is likely at a given time ($t_p$+prediction gap). This process may continue until the end of the mechanical ventilation episode or discharge ($t_e$).

Referring back to FIG. 1, a data processing module 105 receives the data from the data segmentation module 104 and processes the data through a cascade of filters and signal conditioning units to remove measurement and environmental disturbances and noise from the data. As with other elements, steps or processes, in an embodiment the ordering or arrangement of the elements, steps or processes may be changed, such as reordering elements 103 and 104. Different data streams may be processed using a different set of filter banks.

A feature extraction module 106 computes a feature-based representation (e.g., window-based descriptive statistics for each extracted observation window) of the segmented and processed time-series data streams received from the data processing module 105. Furthermore, the feature extraction module 106 represents patient demographics and other irregularly sampled variables such as lab results into a classification-ready format.

A prediction module 107 receives the extracted features representing data samples and determines whether a VAE event is likely to occur within a temporal horizon defined by the prediction gap (see FIG. 2B). The output of the prediction module can be interpreted as a VAE risk score. A risk score may be reported as an indication on an ongoing basis. A risk score exceeding a predetermined threshold may produce a specific type of indication, e.g., an alarm or an alert.

In an embodiment, prior to deployment, the prediction module 107 may be trained and its performance verified using validation procedures, e.g., implemented using a model training and validation module 107a. For example, training and validation procedures may be implemented as a routine that can be repeated periodically or intermittently to ensure the model is in alignment with changes in data reporting models, baselines, care protocols, and CDC guidelines over time. A training and validation routine may include a data set split into train, validation, and test sets and using the train set to train a predictive model. The validation set is used to tune model hyperparameters and the test set is a holdout set, previously unseen by the model, and is used to test the trained model. This process may be repeated a number of times to confirm the stability and performance of the model. The model verification process is often referred to as cross-validation.

In an embodiment, a prediction model implemented using the prediction module 107 may be from any class of machine learning models such as but not limited to: logistic regression, decision trees, or deep learning models. Further, a predictive model directly encoding temporal progression of time-series data (e.g., vital signs, ventilator settings, etc.) such as hidden Markov models or recurrent neural networks and their variations may be used. In the latter, model parameters or resulting time-series abstractions may be combined with other static features such as comorbidities and patient demographics to make the final prediction.

In an embodiment, the prediction module 107 includes a hyperparameter tuning module 107b. The parameters described herein in connection with the data segmentation module 104 (e.g., observation window duration, the amount of overlap (overlap), prediction gap duration, and event window duration) represent a set of hyperparameters of a prediction system. Other hyperparameters may include those specific to a class of machine learning models used e.g., number of decision trees. An optimal setting of these hyperparameters is used for improving prediction model performance and reliably predicting a VAE event. These hyperparameters may be tuned through an outer validation process (outer to the cross-validation for evaluation of model performance) using an optimization routine such as evolutionary algorithms, including particle swarm, as further described herein.

A communication module 110 communicates the prediction results with different endpoints and may take various forms or be provided in different representations. The communication module 110 may include a caregiver-facing dashboard that could be integrated into a monitor, such as patient physiological monitor 111 or a monitor associated with the patient bed 101. In an embodiment, the communication module may provide prediction results to remote or mobile devices, e.g., remotely accessible by the caregivers. In the bedside dashboard, which could be a display on the ventilator 102 itself, a real-time overlay of VAE scores on the ventilator panel may be displayed.

Figure 3:
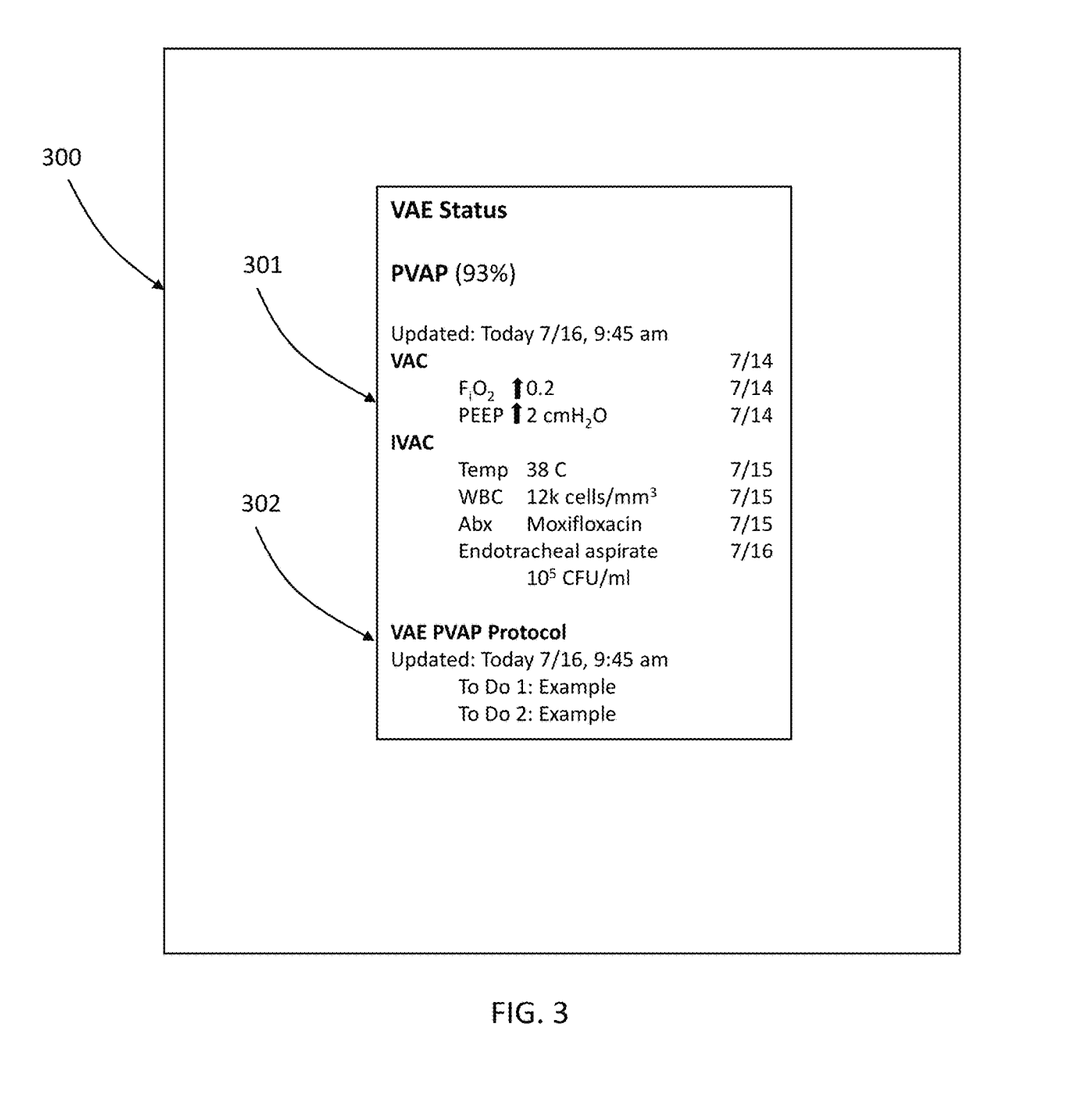
FIG. 3 illustrates an example alert or indication produced by a system that automatically predicts VAEs.

By way of example, as illustrated in FIG. 3, a monitor or display 300 may be configured to include VAE prediction data. In the example of FIG. 3, a window or other display element may include a VAE status, such as a predicted event determined using a prediction model. In the example of FIG. 3, PVAP is predicted with a score of 93%. Additionally, a risk score trend may be displayed. The display may include detailed data 301, e.g., regarding conditions (features) of the patient that are most salient to the VAE status and prediction score. In other scenarios, VAC or IVAC or PVAP or any combination thereof may be predicted. Furthermore, in FIG. 3, for the detected VAC and IVAC events, the most recent values (and their trend), based on which these events are detected, are displayed i.e., increase in daily minimum of $F_iO_2$ and PEEP. Based on this data, PVAP has been predicted. In an embodiment, the display 300 may include a protocol or recommended actions 302, e.g., actions recommended to proactively address the predicted PVAP.

Referring again to FIG. 1, in an embodiment the communication module 110 may communicate or be in the form of a central dashboard (e.g., ICU central station) where the central dashboard displays the most recent VAE risk scores computed for all the mechanically-ventilated patients with an indication, e.g., a flag indicating the patients with a high risk of VAE development and hence in need of intervention. This data allows the caregivers to monitor the patients remotely and attend to those in need of urgent care. In an embodiment, the central dashboard can also display a retrospective, longitudinal view of risk scores for a patient with highlights of relevant signs and biomarkers from different modalities used to compute the scores.

The VAE prediction data may be provided to and displayed on a patient (physiological) monitor 111. The patient monitor 111 monitors and reports patient vitals routinely and in some cases at a set frequency (e.g., respiratory rate, heart rate). This information is used by a clinician to assess patient status. The patient monitor 111 may be equipped to communicate with the communicative module 110, which provides the VAE prediction data (either in raw or aggregated format) with other long-term data, e.g., obtained from EMR 108.

A longitudinal database 109 may be included that stores the computed scores from over time along with highlights of cues and features most-salient to the computed scores. In an embodiment, a VAE prediction model may retrieve stored scores and adjust a patient's baseline accordingly for a more accurate prediction. The longitudinal database 109 may connect to EMR or EHR 108 or other patient management databases with bidirectional communication link to send and retrieve data.

Figure 4:
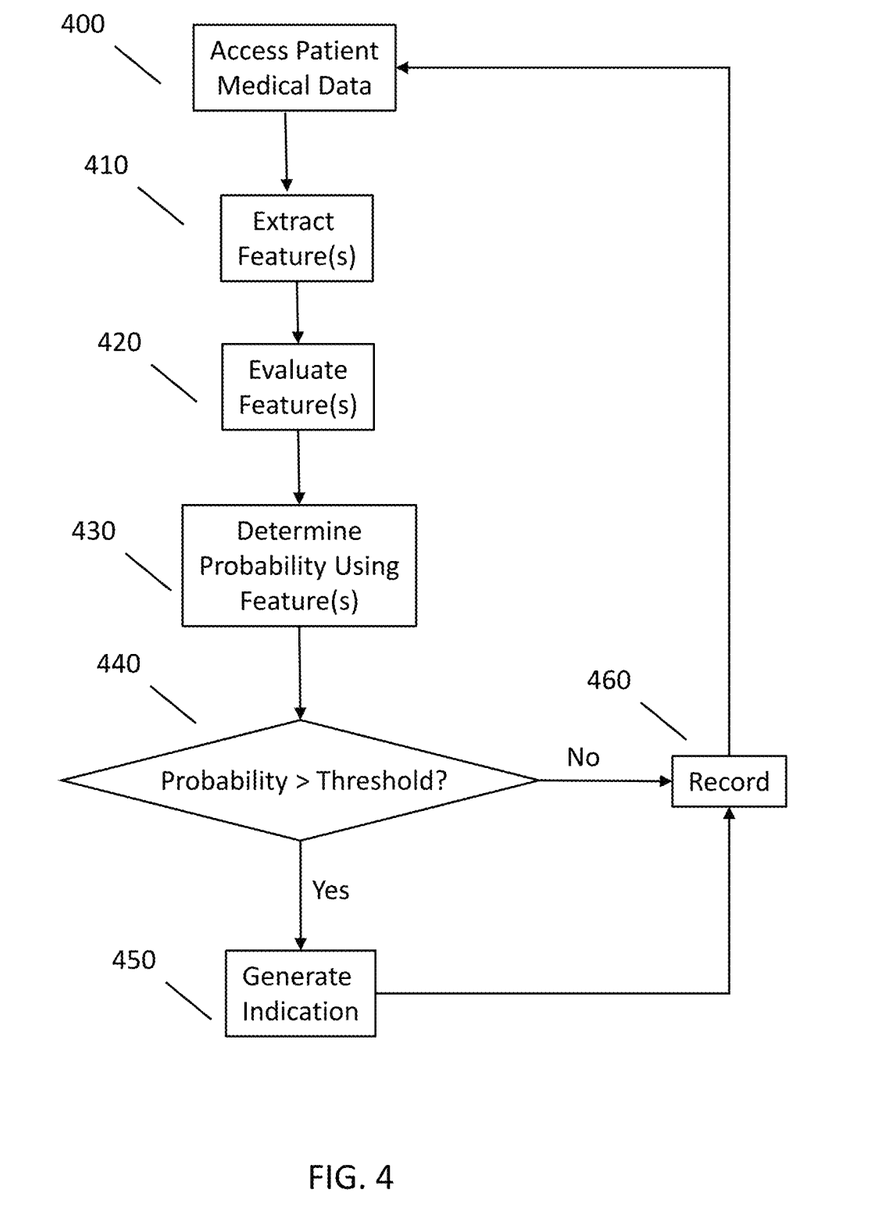
FIG. 4 illustrates an example method for automatically predicting VAEs.

As illustrated in FIG. 4, an embodiment utilizes medical data, e.g., data derived from a ventilator such as ventilator settings, to predict a VAE such as a VAC. In one embodiment, the patient medical data accessed at 400 includes ventilator settings, patient data from an EMR, or a combination of the foregoing. From this data, features are extracted at 410. As described in connection with FIG. 1, data segmentation and processing modules 103, 104 (noting that these and other modules may be combined) may be utilized for feature extraction. In an embodiment, the features extracted at 410 are solely derived from the ventilator, e.g., are ventilator settings or data such as PEEP and $F_iO_2$. In another embodiment, the data may include other data, such as lab results, patient physiological data (e.g., blood pressure, oral hygiene indication, etc.), whether derived from a real time monitor or a medical record. In a further embodiment, the data may include data available prior to or at the onset of MV.

By way of example, accessing of medical data may include use of parameters for extraction of data of interest from the medical data. By way of specific example, a marker may be used to indicate the type of prediction trigger used, e.g., stability, oxygen worsening, or none. When a trigger is set, the data is extracted for a window of time around the trigger, e.g., 48 hours before and after the trigger event. An exclusion parameter may be defined with exclusion criteria, for example an episode length may be configured so that certain data (episodes of less than the episode length) are excluded. Additional parameters such as patient normalization and accounting for missing data may be defined.

The data extraction parameters may be utilized, e.g., by data segmentation module 103, to split patient medical data representing ventilator settings and patient physiology into windows, i.e., observation windows as illustrated in FIG. 2B. Each window represents a set of data from which a probability of VAE occurrence is predicted. In one example, data segmentation parameters such as observation window (time in hours from which features for characterizing the patient status are extracted and used for prediction), window shift (temporal overlap between observation windows, as shown in FIG. 2B), prediction gap (time in hours in advance of a VAE to be predicted, as shown in FIG. 2B), event window (temporal offset in hours around a VAE that is predicted, as shown in FIG. 2B), a marker (a marker of the event that is used to position the event within the event window, e.g., $t_v$, as shown in FIG. 2B), and labeling (indicating how to label extracted samples, e.g., mark a sample as positive if its observation window overlaps with an event window or mark a sample as positive if its corresponding prediction gap overlaps with an event window).

The process of accessing and segmenting the data at 400 may be subjected to an optimization process or routine. An optimization process may include determining which parameters are desirable for use. By way of example, an optimization routine may be utilized to search for a set or combination of segmentation parameters for use by the data segmentation module 103. The suitability of the data segmentation parameters may be evaluated according to a function, for example evaluating parameters against the resultant area under the receiver operating curve (true positive versus false positive) and area under the curve of precision recall (true positive rate vs positive predictive value). By way of specific example, a particle swarm optimization may be used to select a set of observation window, prediction gap and event window parameters. In other embodiments, different optimizers may be used, e.g., a tree-structured Parzen estimator (TPE).

The data accessed at 400 may have features extracted at 410 by a feature extraction module 104. By way of example, extracted, segmented data samples of the patient medical data from the data segmentation module 103 are represented in terms of features that capture descriptive statistics and characterize dynamics of the data streams in each sample (e.g., max, min, median, mean, rate of change). For example, feature types (described below) may be relative over the observation window as compared to a baseline period (e.g., features set to their maximum value minus the mean over a second day of stability (baseline period) to offer patient specific normalization).

By way of specific example, an embodiment may extract one or more of the following features or feature types to use in predicting the probability of a VAE: vitals (vital signs, lab results, care status, e.g., including diastolic blood pressure, ventilator settings, $F_iO_2$, mean blood pressure, PEEP, respiratory rate, peripheral oxygen saturation, systolic blood pressure, temperature, head of bed (angle), glucose (e.g., mg/dL), oral hygiene indication, and urine output), diagnosis (e.g., at admission, international classification of care diagnosis (ICD) codes), type of ICU, demographics (e.g., height, weight, gender), binary flags (e.g., indication of oral hygiene, sedative drug administration), peak inspiratory pressure (PIP), Pplateau (plateau pressure), tidal volume, Glasgow coma scores (e.g., total, eye movement, verbal, motor), other lab results (e.g., albumin, pH, hematocrit, oxygen saturation, partial pressure of oxygen, sodium, blood urea nitrogen, white blood cell count, bicarbonate, chloride, hemoglobin, lactate, platelet count, creatinine, potassium, lymphocytes), and temporal features (e.g., describing temporal progress such as the day and hour of mechanical ventilation and stability offset, capturing the distance of observation windows to the stability marker, e.g., of the trigger event or other stability period time). As will be appreciated, the nature and types of features and their extraction and representation may be modified, e.g., based on data availability and format or the model utilized.

Figure 5A:
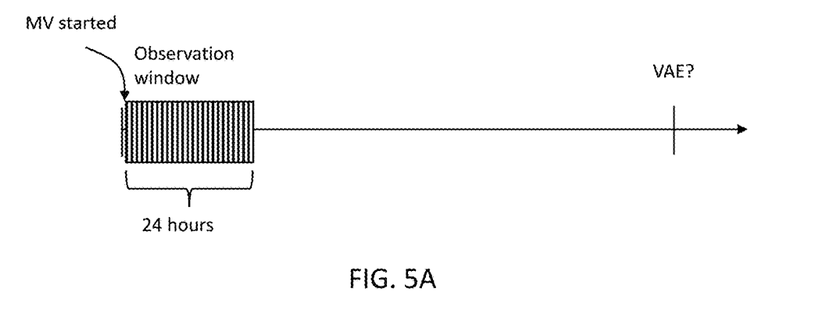
FIG. 5A and FIG. 5B illustrate examples related to a VAE early warning system.
Figure 5B:
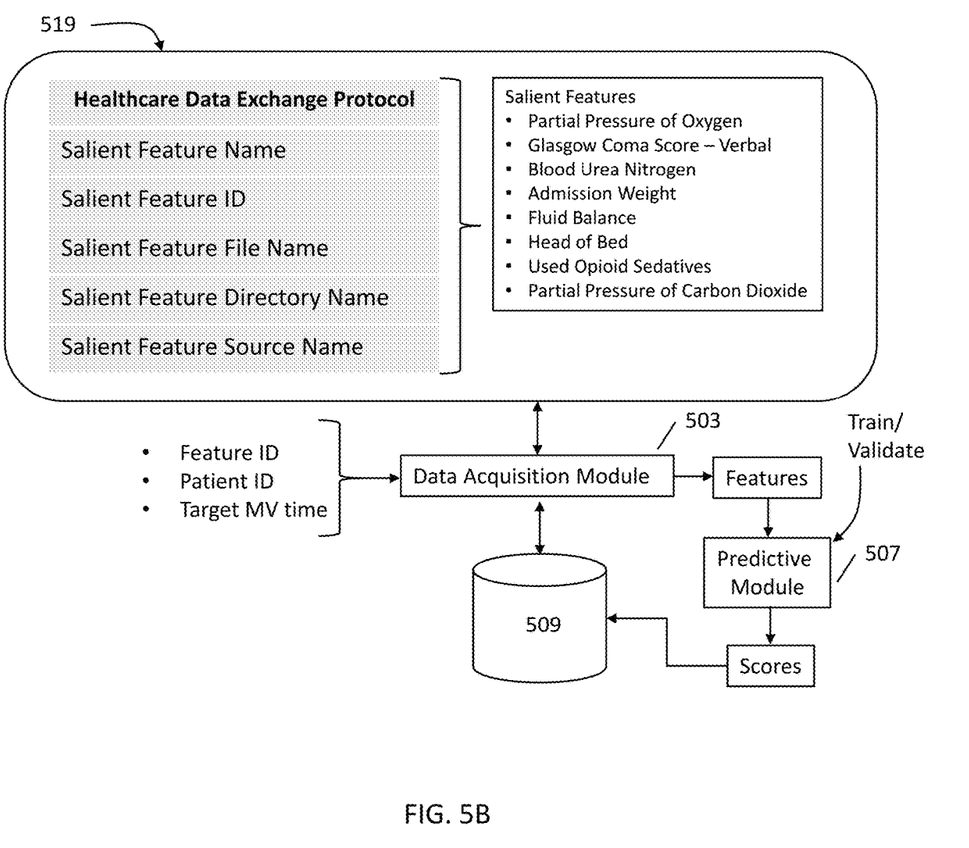

The extracted features are evaluated by a prediction model at 420. The prediction model in one example is a trained model, e.g., trained on prior data to learn to weight the features important for predicting a VAE. By way of example, the trained model used at 420 may be a model trained and configured to utilize data from a ventilator alone. In another example, the trained model used at 420 may be trained and configured to utilize data from the ventilator and another data source, such as an EMR. In a further embodiment, the trained model used at 420 may be trained and configured to utilize data available prior to or at the onset of MV, e.g., data from an EMR, as described in connection with FIG. 5(A-B). In an embodiment, the trained prediction model may be a gradient boosted trees type classifier, e.g., XGBoost. In other embodiments, the trained prediction model may be another type of classifier, e.g., regularized binomial logistic regression or random forest.

In an embodiment, the classifier used at 420 is trained using a training data set and training routine suitable for the classifier type. By way of specific example, medical data may be separated into training, validation and test sets. For example, a data set is used to train a classifier and a data set is used to validate the classifier. In training iterations, the training data is extracted, segmented and features are extracted. This process is repeated to allow for feature scaling, classifier training, and internal validation. Once a classifier has been validated, it may be tested and evaluated against performance metrices, e.g., area under the curve, on a set aside and previously unseen test set. The trained classifier represents a trained model that may be used to classify similar data, i.e., may be provided to a ventilator or associated device and thereafter used to evaluate the patient medical data streamed in at 420 in order to predict a VAE.

As may be appreciated, because different classifiers may be chosen, and these classifiers may be trained using different data sets, it is not practical to predict exactly which features may be most important in influencing any given model's performance. However, for an example XGBoost classifier trained on medical data from Medical Information Mart for Intensive Care (MIMIC) III, $FiO_2$, stability offset (temporal parameter capturing the distance of observation windows to the stability marker), and PEEP were found to be of particular usefulness in accurately predicting a VAE. This example model was prepared using particle swarm optimization to find a set of tuned hyperparameters: observation window of 4 hours, predication gap of 20 hours, and event (prediction) window of 7 hours (refer to FIG. 2B).

As shown in FIG. 4, the features are evaluated to determine a probability score for a VAE at 430, e.g., a VAC score as shown in FIG. 2A. When a VAE score for a patient passes a set threshold, as determined at 440, an indication may be generated and provided, as indicated at 450. This allows caregivers to be notified to promote timely and personalized treatment regiments such as titration of medications and/or spontaneous breathing trial. As described in connection with example of FIG. 3, the reported risk score(s) or associated data may be accompanied with recommendation on interventions. In any event, e.g., even if an indication such as an alarm is not generated, the resultant score(s) or other data associated therewith may be recorded at 460, e.g., to an EMR or database.

Referring to FIG. 5A, an embodiment may be used to evaluate a patient prior to MV or at the onset of MV, e.g., in the first 24 hours. By way of example, as illustrated in FIG. 5A, at the start of MV an observation window, e.g., 24 hours, is specified to obtain data that is used to make a prediction with respect to the probability of occurrence of a future VAE, e.g., days later. Such an embodiment may be used as an early warning system to deliver recommendations on intervention(s) along with notifications about high-risk patients at the beginning or early during the course of MV. As may be appreciated, this embodiment may be combined with others, e.g., to provide ongoing risk scores during the course of MV.

Referring to FIG. 5B, a prediction module 507 that implements a prediction model for early warning receives patient medical data in the form of salient features from a data acquisition module 503. The feature data may be stored in a salient feature library 519. The salient feature library 519 provides storage for keeping a record of salient features for identifying high-risk patients. The prediction module 507 reads the features from the feature library 519, e.g., directly or indirectly (via data acquisition module 503). Along with each feature, the feature library 519 may store information related to where the feature in its raw or abstracted format resides. New features can be written to the feature library 519. In embodiments, patient cohorts based on demographics and comorbidities can be created and cohort-specific features can be created. The salient features may be stored in a common or standardized format, e.g., Healthcare Data Exchange Protocol, and include a feature name, feature ID, file name, directory name, and source name (e.g., EMR). Non-exhaustive examples of salient features include one or more of partial pressure of oxygen, Glasgow Coma Score (verbal), blood urea nitrogen, admission weight, fluid balance, head of bed, used opioid sedatives, and partial pressure of $CO_2$.

Given feature ID(s), a patient ID, and target MV time (e.g., 24 hours), the data acquisition module 503 obtains the indicated data, e.g., from feature library 519. The data acquisition module 503 provides features that are used by the prediction module 507 to produce VAE risk score(s). The scores may be stored back to a database 509 as well as communicated, e.g., via a server or other communication module, to various endpoints such as a ventilator display screen, caregiver devices, central dashboard, etc.

The data acquisition module 503 reads the salient feature(s) from the salient feature library 519 and retrieves them from their corresponding path (e.g., EMR, ventilator, etc.). For example, the data acquisition module 503 may include a communication link to a ventilator, e.g., ventilator 102, EMR, and various databases or data sources (collectively indicated at 509), to retrieve data related to the salient features. The data acquisition module 503 may use standard protocols and API's (e.g., Fast Healthcare Interoperability Resources (FHIR)) to communicate and extract data from the data sources.

For a given patient ID, the data acquisition module 503 receives the associated start time of the MV episode and queries the salient features using feature ID(s) for the target MV time window (target MV time in FIG. 5B). The target MV time indicates the window based on which the risk assessment is performed. By way of example, a default value for the target MV time is the first 24 hours of MV (observation window of FIG. 5A). As described herein, the data acquisition module 503 may also process the data through a set of standard filters and signal conditioning units to remove measurement and environmental disturbances and noise, if needed.

The prediction module 507 receives the retrieved salient features for a patient and the target MV time and estimates the patient's risk of VAE, which may be output as a score. Prior to deployment and periodically after deployment, this prediction module 507 may be trained (and thereafter retrained), and have its performance verified using validation procedure(s). The training and validation procedures constitute a routine that can be repeated periodically to ensure the model used by prediction module 507 is in alignment with changes in data reporting models, baselines, and CDC guidelines over time. As described herein, a training and validation routine includes a data split into training, validation, and test sets at the patient level and uses a training set to train a predictive model. The validation set is used to tune the model parameters and the test set is a holdout set previously unseen by the model and is used to test the trained model. This process may be repeated a number of times to confirm the stability and performance of the model. As with other embodiments, the prediction module used may take a variety of forms, e.g., may be from a class of conventional predictive models (e.g., logistic regression, decision trees) or deep learning models. Further, predictive models directly encoding temporal progression of time-series data (e.g., vital signs, ventilator settings) such as hidden Markov models or recurrent neural networks and their variations may be used.

Figure 6:
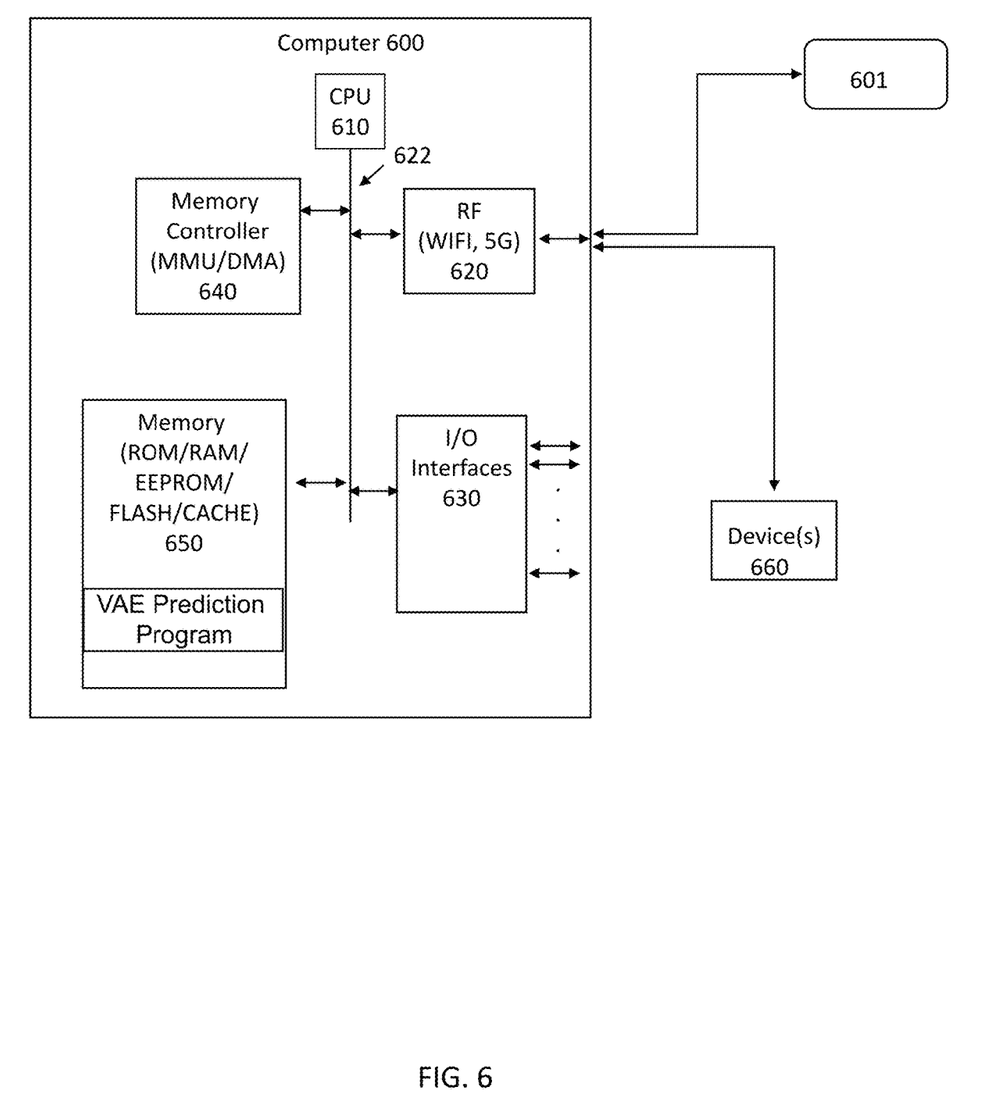
FIG. 6 illustrates an example system in accordance with an embodiment.

Referring to FIG. 6, it will be readily understood that certain embodiments can be implemented using any of a wide variety of devices or combinations of devices. In FIG. 6 an example system on chip (SoC) included in a computer 600 is illustrated, which may be used in implementing one or more embodiments, e.g., as a device used to implement a VAE prediction process as described herein. The SoC or similar circuitry outlined in FIG. 6 may be implemented in a variety of devices, for example similar circuitry may be included in ventilator device 102, as part of a communication module 110, or another device or platform. In addition, circuitry other than a SoC, an example of which is provided in FIG. 6, may be utilized in one or more embodiments. The SoC of FIG. 6 includes functional blocks, as illustrated, integrated onto a single semiconductor chip to meet specific application requirements.

The central processing unit (CPU) 610, which may include one or more graphics processing units (GPUs) and/or micro-processing units (MPUs), includes an arithmetic logic unit (ALU) that performs arithmetic and logic operations, instruction decoder that decodes instructions and provides information to a timing and control unit, as well as registers for temporary data storage. The CPU 610 may comprise a single integrated circuit comprising several units, the design and arrangement of which vary according to the architecture chosen.

Computer 600 also includes a memory controller 640, e.g., comprising a direct memory access (DMA) controller to transfer data between memory 650 and hardware peripherals. Memory controller 640 includes a memory management unit (MMU) that functions to handle cache control, memory protection, and virtual memory. Computer 600 may include controllers for communication using various communication protocols (e.g., $I^2C$, USB, etc.).

Memory 650 may include a variety of memory types, volatile and nonvolatile, e.g., read only memory (ROM), random access memory (RAM), electrically erasable programmable read only memory (EEPROM), Flash memory, and cache memory. Memory 650 may include embedded programs and downloaded software, e.g., software such as a VAE prediction program. By way of example, and not limitation, memory 650 may also include an operating system, application programs, other program modules, and program data, which may be downloaded, updated, or modified via remote devices such as device(s) 660. In one example, an application or program module such as a VAE prediction module may be downloaded or updated over a network or data connection. Such a technique may be used to initiate or install a prediction module, e.g., using data from another ventilator, to update or change an existing prediction module, e.g., for another patient population, etc.

A system bus 622 permits communication between various components of the computer 600. I/O interfaces 630 and radio frequency (RF) devices 620, e.g., WIFI and telecommunication radios, may be included to permit computer 600 to send and receive data to and from remote devices using wired or wireless mechanisms. The computer 600 may operate in a networked or distributed environment using logical connections to one or more other remote computers or databases. The logical connections may include a network, such local area network (LAN) or a wide area network (WAN), but may also include other networks/buses. For example, computer 600 may communicate data with and between a ventilator 102 and other devices, e.g., a patient monitor 111, a database 109, caregiver devices 601, or other remote device(s) 660, etc.

The computer 600 may therefore execute program instructions configured to store and analyze patient medical data related to ventilated patient conditions within an ICU context in order to predict a VAE and perform other functionality of the embodiments, as described herein. A user can interface with (for example, enter commands and information) the computer 600 through input devices, which may be connected to I/O interfaces 630. A display or other type of device may be connected to the computer 600 via an interface selected from I/O interfaces 630.

It should be noted that the various functions or modules described herein may be implemented using instructions or code stored on a memory, e.g., memory 650, that are transmitted to and executed by a processor, e.g., CPU 610. Computer 600 includes one or more storage devices that persistently store programs and other data. A storage device, as used herein, is a non-transitory computer readable storage medium. Some examples of a non-transitory storage device or computer readable storage medium include, but are not limited to, storage integral to computer 600, such as memory 650, a hard disk or a solid-state drive, and removable storage, such as an optical disc or a memory stick.

Program code stored in a memory or storage device may be transmitted using any appropriate transmission medium, including but not limited to wireless, wireline, optical fiber cable, RF, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In an embodiment, program code may be stored in a non-transitory medium and executed by a processor to implement functions or acts specified herein. In some cases, the devices referenced herein may be connected through any type of connection or network, including a local area network (LAN) or a wide area network (WAN), or the connection may be made through other devices (for example, through the Internet using an Internet Service Provider), through wireless connections or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions (computer code) may be provided to a processor of a device to produce a special purpose machine, e.g., a ventilator with VAE prediction capabilities, such that the instructions, which execute via a processor of the device implement the functions/acts specified.

It is worth noting that while specific elements are used in the figures, and a particular ordering of elements has been illustrated, these are non-limiting examples. In certain contexts, two or more elements may be combined, an element may be split into two or more elements, or certain elements may be re-ordered, re-organized, or omitted, as appropriate, as the explicit illustrated examples are used only for descriptive purposes and are not to be construed as limiting.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method of predicting ventilator associated events, comprising:
    using one or more processors to execute a segmentation module comprising executable code configured to:
        access time series data of a patient from a ventilator, the time series data comprising one or more features;
        identify a trigger event in the time series data comprising one or more of a stability period and an oxygen worsening event; and
        segment the time series data into observation windows based on the trigger event and a set of tuned hyperparameters comprising one or more of observation window duration, observation window overlap, prediction gap, and future event window duration;
    using the one or more processors to execute a feature extraction module comprising executable code configured to compute a feature-based representation of the segmented time series data, extracting the one or more features for each of the observation windows into a standard format;
    using the one or more processors to operate a trained classification model configured to evaluate, for each of the observation windows, the one or more features to determine a probability that a ventilator-associated event (VAE) will occur in a future event window associated with a respective one of the observation windows;
    determining, using the one or more processors, based on output of the trained classification model, that a predicted VAE has a probability of occurring that exceeds a threshold;
    providing, using an output device operatively coupled to the ventilator, an indication that the predicted VAE is predicted to occur for the patient in the future event window; and
    proactively providing, based on the indication, a spontaneous breathing trial in advance of the predicted VAE.

2. The method of claim 1, wherein the one or more features include one or more of positive end-expiratory pressure (PEEP) and fraction of inspired oxygen ($FiO_2$).

3. The method of claim 2, wherein the one or more features include one or more of lab results and patient physiological data.

4. The method of claim 1, wherein the indication is one or more of a score, a color, an audible alert, and a recommendation.

5. The method of claim 4, wherein the providing comprises providing data configured to display the indication on a display device associated with one or more of: the ventilator, a patient monitor, a central monitor and a remote device.

6. The method of claim 1, comprising:
    displaying one or more recommended actions responsive to the indication that the predicted VAE is predicted to occur for the patient in the future event window.

7. The method of claim 1, comprising titrating medicine for the patient based on the predicted VAE.

* * * * *